United States Patent [19]

Starr

[11] Patent Number: 4,886,642
[45] Date of Patent: Dec. 12, 1989

[54] MEASUREMENT OF TOTAL IRON BINDING CAPACITY

[76] Inventor: Ross T. Starr, 74 Baillie Street, Horsham, Victoria, Australia

[21] Appl. No.: 176,265

[22] Filed: Mar. 31, 1988

Related U.S. Application Data

[62] Division of Ser. No. 885,568, May 6, 1986, Pat. No. 4,735,904.

[30] Foreign Application Priority Data

Nov. 7, 1984 [AU] Australia ............................. PG8017
Nov. 20, 1984 [AU] Australia ............................. PG8209

[51] Int. Cl.$^4$ .......................................... G01N 33/20
[52] U.S. Cl. ...................................... 422/58; 422/57; 436/74; 436/84; 436/910
[58] Field of Search .................. 422/57, 58; 436/74, 436/84, 165, 808, 910, 800

[56] References Cited

U.S. PATENT DOCUMENTS

| | | | |
|---|---|---|---|
| 3,537,822 | 11/1970 | O'Malley et al. | 23/230 B |
| 3,773,467 | 11/1973 | Yang et al. | 23/230 B |
| 3,887,332 | 6/1975 | Jakase et al. | 23/230 B |
| 3,900,122 | 8/1975 | Dichter | 215/355 |
| 3,925,020 | 12/1975 | Ogawa et al. | 23/230 B |
| 4,224,034 | 9/1980 | Denney et al. | 23/230 B |
| 4,227,620 | 10/1980 | Conway | 215/355 |
| 4,233,031 | 11/1980 | Matson et al. | 23/230 B |
| 4,272,478 | 6/1981 | Vikho | 422/58 |
| 4,308,027 | 12/1981 | Ceriotti | 23/230 B |
| 4,434,235 | 2/1984 | Rabi et al. | 422/58 |
| 4,522,923 | 6/1985 | Deutsch et al. | 422/58 |
| 4,567,150 | 1/1986 | Tabacco et al. | 436/84 |
| 4,588,695 | 4/1986 | Takano et al. | 436/84 |
| 4,608,231 | 8/1986 | Wilty et al. | 422/61 |
| 4,624,929 | 11/1986 | Ullman | 436/179 |

FOREIGN PATENT DOCUMENTS 0061793 6/1982 European Pat. Off.

OTHER PUBLICATIONS

Ramsay, W. N. M., The Determination of the Total Iron Binding Capacity of Serum, Clin. Chim. Acta 2, 221 (1957).
Peters, T., Giovanniello, T. J., Apt L., and Ross, J. R., A New Method for the Determination of Serum Iron Binding Capacity, J. Lab. Clin. Med. 48, 274 (1956).
Williams, H. L. and Conrad, M. E., A One-Tube Method for Measuring the Serum Iron Concentration and Unsaturated Iron Binding Capacity, J. Lab. Clin. Med. 67, 171 (1966).
Starr, R. T., Use of an Alumina Column in Estimating Total Iron-Binding Capacity, Clin. Chem. 26, 156 (1980).
Ramsay, W. N. M., The Measurement of Serum Transferring by Iron-Binding Capacity, J. Clin. Pathol. 26, 691 (1973).
Cook, J. D., An Evaluation of Adsorption Methods for Measurement of Plasma Iron-Binding Capacity, J. Lab. Clin. Med. 76, 497 (1970).
Dixon, K., Routine Clinical Measurement of Transferring in Human Serum, Ann. Clin. Biochem., 10, 127 (1973).
Klein, B., Lucas, L. B., Searey, L., Application of Fe(II)-5-Pyridyl Benzediazepin-2-Ones to the Determination of Serum Iron-Bonding Capacity, Clin. Chem. Acta. 26, 517 (1969).
Whicher, J. T., Blow, C., Formulation of Optimal Conditions for an Immunonephelometric Assay, Ann. Clin. Biochem. 17, 170 (1980).
Bandi, Z. L., Schoen, I., Bee, D., Immunochemical Methods for Measurement of Transferring in Serum: Effects of Analytical Errors and Inappropriate Reference Intervals on Diagnostic Utility, Clin. Chem. 31, 1601 (1985).
International Committee for Standardization in Haematology, The Measurement of Total and Unsaturated Iron-Binding Capacity in Serum, British Journal of Haematology 38, 281 (1978).

Primary Examiner—Barry S. Richman
Assistant Examiner—Lyle Alfandary-Alexander
Attorney, Agent, or Firm—Roylance, Abrams, Berdo & Goodman

[57] ABSTRACT

An apparatus for use in the measurement of total iron binding capacity of blood serum or plasma comprises a container having a removable closure and containing a measured quantity of dried iron-saturating substance, which is adhered to the inner surface of the container or of the closure and a measured quantity of dried alumina. The invention further provides a simple, rapid and inexpensive method for measurement of total iron binding capacity using the apparatus.

20 Claims, 1 Drawing Sheet

MEASUREMENT OF TOTAL IRON BINDING CAPACITY

This is a division of application Ser. No. 885,568 filed May 6, 1986 now U.S. Pat. No. 4,735,904.

BACKGROUND OF THE INVENTION

This invention relates to the measurement of total iron binding capacity in serum.

Iron is carried in the blood plasma by a specific carrier protein called transferrin. This is a protein of molecular weight 76,000–80,000, which has two sites each capable of binding one iron atom. The total amount of transferrin present determines the total iron binding capacity (T.I.B.C.) of the serum.

The estimation of the T.I.B.C. is an important clinical procedure, with an established role in the diagnosis of such conditions as iron deficiency anaemia and haemochromatosis, and in the monitoring of therapeutic procedures. In iron deficiency states, T.I.B.C. is elevated; in iron overload conditions T.I.B.C. is depressed.

Techniques which are currently used for determination of T.I.B.C. rely on the saturation of transferrin and removal of excess iron from the serum with an adsorbent such as magnesium carbonate (Ramsay, W. N. M.: Clin. Chim. Acta 2 221 (1957)) or an ion exchange resin (Peters, T., Giovanello T. J., Apt, L. and Ross, J. R.; J. Lab. Clin. Med. 48 274 (1956)). Other methods employ direct measurement of the excess iron after saturation, and calculation of unsaturated iron-binding capacity (Williams, H. L., and Conrad, M. E.; J. Lab. Clin. Med. 67 171 (1966); O'Malley, J. A., Hassan, A., Shiley, J., and Traynor, H.; Clin. Chemistry 16 92 (1970)). The most commonly used magnesium carbonate method is subject to error owing to the inclusion of non-transferrin bound iron in the supernatant solution (Ramsay, W. N. M.; J. Clin. Pathol. 26 691 (1973)).

An improved method using an alumina column, which was faster and simpler than the magnesium carbonate method while offering improved accuracy, was previously disclosed by the present inventor (Clin. Chemistry 26 156 (1980)).

SUMMARY AND OBJECTS OF THE INVENTION

The object of the present invention is to provide improvements in the measurement of T.I.B.C.

There is provided in accordance with the invention a tube closed at one end, having a removable closure, the tube containing a measured quantity of a dried iron-saturating substance, which is adhered to the inner surface of the base of the tube, and a measured quantity of dried alumina (aluminium oxide, $Al_2O_3$).

Preferably the tube and closure are made of plastics.

Preferably the neck of the plastic tube is threaded to receive a plastics screw cap. The screw cap is most preferably large enough to contain the quantity of alumina.

Preferably the tube is made of polystyrene, most preferably of transparent polystyrene.

Preferably the cap is made of polyethylene.

The dried iron-saturating substance is preferably a complex salt of ferric iron.

The alumina is preferably basic chromatographic grade alumina, most preferably Brockmann grade II.

Preferably the tube is designed to fit sample carriers of automatic analysers such that their sample probes will sample from above the level occupied by alumina in the tube.

According to a further aspect of the invention, there is provided a method of performing the measurement of T.I.B.C. using the apparatus described hereinabove comprising pouring alumina out of the tube into the cap, adding a solvent, for example water, to the tube to dissolve the iron-saturating substance, and adding the sample of serum to the tube; then after a brief period of incubation to allow the iron to bind to transferrin in the serum sample, replacing the alumina in the tube, mixing the tube to allow binding of the unbound iron to the alumina, and after allowing the alumina to settle, measuring the iron content of the supernatant by any suitable means, for example by automatic continuous flow analyser or by atomic absorption spectroscopy.

BRIEF DESCRIPTION OF THE FIGURES OF THE DRAWING

Preferred embodiments of the invention will now be described by way of example only with reference to the accompanying drawings in which.

DETAILED DESCRIPTION OF THE PREFERRED EMBODIMENTS

Figures 1, 2, 3:
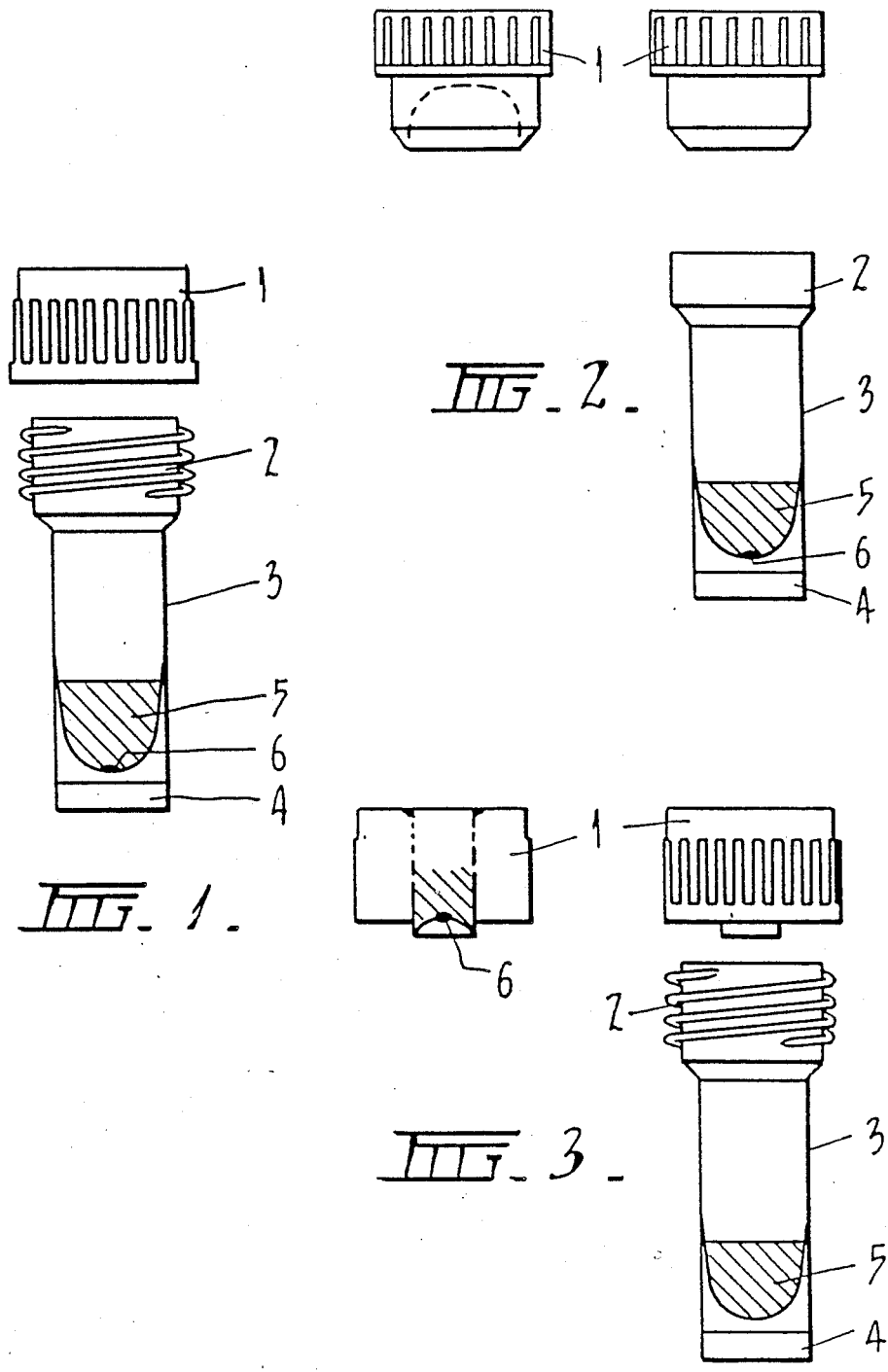
FIG. 1 represents an exploded view of a free-standing sample tube having a screw cap, containing a measured amount of alumina powder, and having a measured amount of an iron-saturating substance bonded to the interior surface of the tube.
FIG. 2 represents an exploded view of free-standing sample tube as in FIG. 1 but having a slidably fitting cap.
FIG. 3 represents an exploded view of a free-standing sample tube as in FIG. 1, but having a screw cap with a solid central projection extending to a hollow opening, to the interior surface of which is bonded a measured amount of an iron-saturating substance.

According to one embodiment of the invention there is provided a free-standing sample tube as shown in FIG. 1 comprising a polyethylene cap 1 which is adapted to screw onto the threaded neck 2 of a polystyrene tube 3 which is closed at one end, and has a rim 4 forming a base which enables the tube to be free-standing. The tube contains a measured amount of washed and dried chromatographic-grade alumina powder 5, and a measured amount of an iron-saturating substance 6 bonded to the base of the interior surface of the tube 3.

According to one preferred embodiment there is provided a free-standing sample tube, comprising a polyethylene cap 1 which is adapted to fit snugly within the neck 2 of a polystyrene tube 3 which is closed at one end, and has a rim 4 forming a base which enables the tube to be free-standing. The tube contains a measured amount of washed and dried chromatographic-grade alumina powder 5, and a measured amount of an iron-saturating substance 6 bonded to the base of the interior surface of the tube 3.

The polyethylene cap defines a hemispherical enclosure large enough to contain the alumina and constructed so that the internal diameter of the cap is identical to that of the base. The cap is designed to fit into the base such that there is a continuous, unbroken internal surface.

The tube preferably is 44 mm high (not including the cap), has an outside diameter of 15 mm at the top and 12.5 mm at the base, and has a working capacity of 2 ml. More preferably the tube is 40 mm high.

Preferably 0.4 g of alumina is used.

In a preferred embodiment, the iron-saturating substance is attached to the base of the tube 3 by adding 10 ul of a solution of $FeCl_3$ at a concentration of 500 mg $Fe^{3+}/l$ in 0.1 mole/l citric acid containing 0.2% sodium azide and heating the tube in an oven at 70° until dry (approximately 3 hours).

In a specific example, the test is performed as follows:
1. Invert the tube and remove the cap so that the alumina is retained in the cap.
2. Add 1 ml. of water to the tube and wait two minutes or longer to dissolve the dried iron saturating substance which is attached to the bottom of the tube.
3. Add 0.5 ml. of specimen (serum) and stand three minutes or longer to allow the iron to bind to the carrier protein transferrin.
4. Pour the alumina back into the tube and then replace the cap.
5. Place the capped tube onto a laboratory rotator and mix by constant inversion for ten minutes or longer.
6. Remove the tube from the rotator and stand ½ minute or longer and either transfer a portion of the supernatant to another sample container or use the tube itself as a sample container. (The tube may be used as the sample container on some automatic instruments e.g. the Technicon auto-analysers commonly used in hospitals.
7. Measure the iron content of the supernatant.

According to another preferred embodiment, there is provided a free standing sample tube as shown in FIG. 3, comprising a polyethylene cap 1 which is adapted to screw onto the threaded neck 2 of a polystyrene tube 3 which is closed at one end and has a rim 4 forming a based which enables the tube to be free standing. The tube contains a measured amount of washed and dried chromatographic-grade alumina powder 5.

The cap 1 contains a solid central projection which extends to a hollow opening, which may for example be hemispherical. A measured amount of an iron-saturating substance 6 is bonded to the interior surface of the opening.

This cap design allows the test to be performed without decanting the alumina. The central projection to which the iron-saturating substance is bonded restricts contact of alumina with the iron-saturating substance, thereby allowing iron to dissolve and bind to transferrin before it is bound to alumina.

The tube preferably is 44 mm high (not including the cap), has an outside diameter of 15 mm at the top and 12.5 mm at the base and has a working capacity of 2 ml. The central projection has an external diameter of 7 mm and extends 11 mm into the tube when the cap is screwed on. The hollow opening of the projection is able to contain 10 ul of solution.

The iron-saturating substance is attached to the interior of the hollow opening by adding 10 ul of a solution of $FeCl_3$ at a concentration of 500 mg $Fe^{3+}/l$ in 0.45 mole/l citric acid containing 1% glycerol to the inverted caps and heating at 70° C. in an oven until dry (approximately three hours). The concentration of citric acid (0.45 mole/l) is chosen to promote optimum binding or iron to transferrin in the presence of alumina. The glycerol is added to enhance bonding of the iron-saturating substance to polyethylene.

Preferably 0.4 g of alumina is used.

In a specific example the test is performed as follows:

1. Remove the cap containing the iron-saturating substance.
2. To the tube containing the alumina add 1 ml of water followed by 0.5 mls of serum.
3. Replace cap and proceed with steps 5 to 7 as before.

The present invention represents a considerable improvement compared to the prior art with respect to the cost of materials, stability of reagents, speed and convenience of carrying out the procedure, and reliability of results. The cost of materials for the present invention is less than one third the cost for the column technique. The prepared tubes are stable for at least six months at room temperature, compared to the stability of the stock $FeCl_3$ solution of the present inventor's earlier publication (Clin. Chemistry 26 156 (1980)) which was three months at 4° C. The working solution in that case was stable for one week only. The procedure of the present invention can be performed in one minute (excluding the incubation period), compared to 1½ minutes for the earlier procedure.

Furthermore, a considerable amount of labour is avoided by the provision of the reagents in pre-packaged form, eliminating the need for washing and drying and weighing or dispensing of alumina and preparation and dispensing of iron solution for the column method.

Quality control for the procedure can be enhanced by the pre-testing of batches of alumina before addition to the tubes. This overcomes the problem of the occasional batch of alumina which binds iron inconsistently, leading to errors and further expense.

Thus the use of the "one-tube" technique of the present invention results in cost savings in both materials and labour.

The procedure of the present invention is not subject to error resulting from lipaemic, icteric or haemolysed serum samples. Preliminary studies indicate that the procedure is applicable to plasma samples as well as to serum samples.

It will be clearly understood that the invention in its general aspects is not limited to the specific details referred to hereinabove.

I claim:

1. A self-contained, one-tube article of manufacture for measuring the total iron binding capacity of blood serum or plasma comprising a container having a closed end, an open end and a liquid impermeable removable closure for forming a liquid impermeable seal between the container and closure, wherein the container is pre-packaged to contain a measured quantity of a dried iron-saturated substance bonded to the interior surface of the container and a measured quantity of dried alumina, wherein the closure includes means for containing said measured quantity of alumina.

2. An article of manufacture according to claim 1, in which the tube is made of polystyrene.

3. An article of manufacture according to claim 1, in which the dried iron-saturating substance is a complex salt of ferric iron.

4. An article of manufacture according to claim 1, in which the alumina is basic chromatographic grade alumina.

5. An article of manufacture according to claim 1, in which the alumina is of Brockmann grade II.

6. An article of manufacture according to claim 1, in which the tube and closure are made of plastics.

7. An article of manufacture according to claim 6, in which the neck of the plastic tube is threaded to receive said closure in the form of a plastic screw cap.

8. An article of manufacture according to claim 7, in which the screw cap is large enough to contain the quantity of alumina.

9. An article of manufacture according to claim 7, in which the cap is made of polyethylene.

10. A self-contained, one-tube article of manufacture for use in the measurement of total iron binding capacity of blood serum or plasma, comprising a liquid impermeable polyethylene cap which is adapted to fit forming a liquid impermeable seal within the neck of a polystyrene tube which is closed at one end, and has a rim forming a base which enables the tube to be free standing, in which the tube is pre-packaged to contain a measured amount of washed and dried basic chromatographic grade alumina powder, and a measured amount of an iron-saturating substance bonded to the base of the interior surface of the tube, wherein the polyethylene cap defines a hemispherical enclosure open to the interior of the tube large enough to contain the alumina and constructed so that the internal diameter of the cap is identical to that of the base, the cap being designed to fit into the base such that there is a continuous, unbroken internal surface.

11. A self-contained, one-tube article of manufacture for use in the measurement of total iron binding capacity of blood serum or plasma, comprising a liquid impermeable polyethylene cap which is adapted to screw on to the threaded neck of a polystyrene tube which is closed at one end forming a liquid impermeable seal and has a rim forming a base which enables the tube to be free standing, in which the tube is pre-packaged to contain a measured amount of washed and dried basic chromatographic grade alumina powder, and further characterized in that the cap contains a solid central projection which extends to a hemispherical hollow opening. in which a measured amount of an iron-saturating substance is bonded to the interior surface of the projection.

12. An article of manufacture according to claim 11, in which the central projection has an external diameter of 7 mm and extends 11 mm into the tube when the cap is screwed on, such that the hollow opening of the projection is able to contain 10 ul of solution.

13. An article of manufacture according to claim 11, in which iron-saturating substance is attached to the interior of the hollow opening by adding 10 ul of a solution of $FeCl_3$ at a concentration of 500 mg $Fe^{3+}$/l in 0.45 mole/l citric acid containing 1% glycerol to the inverted caps and heating at 70° C. in an oven until dry.

14. A self-contained, one-tube article of manufacture for use in the measurement of total iron binding capacity of blood serum or plasma, comprising a liquid impermeable polyethylene cap which is adapted to form a liquid impermeable seal by screwing onto a threaded neck of a polystyrene tube which is closed at one end with a rim forming a base which enables the tube to be free-standing, wherein the tube is pre-packaged to contain a measured amount of washed and dried basic chromatographic grade alumina powder and a measured amount of iron-saturating substance bonded to the base of the interior surface of the tube, wherein the cap includes means for containing the measured of alumina powder.

15. An article of manufacture according to claim 14, in which the amount of alumina is 0.4 g.

16. An article of manufacture according to claim 14, in which the iron-saturating substance is attached to the base of the tube by adding 10 ul of a solution of $FeCl_3$ at a concentration of 500 mg $Fe^{3+}$/l in 0.1 mole/l citric acid containing 0.2% sodium azide and heating the tube in an oven at 70° C. until dry.

17. An article of manufacture according to claim 14, in which the tube is of a size adapted to fit the sample carrier of an automatic analyser such that the sample probe of the analyser will sample from above the level of alumina in the tube.

18. An article of manufacture according to claim 14, in which the tube is 40–45 mm high (not including the cap), has an outside diameter of 15 mm at the top and 12.5 mm at the base, and has a working capacity of 2 ml.

19. An article of manufacture according to claim 18, in which the tube is 40 mm high.

20. A one-tube method for measurement of total iron binding capacity using a self-contained, one-tube article of manufacture for use in the measurement of total iron binding capacity of blood serum or plasma, comprising a liquid impermeable polyethylene cap which is adapted to screw on the threaded neck of a polystyrene tube which is closed at one end forming a liquid impermeable seal and has a rim forming a base which enables the tube to be free standing, in which the tube is prepackaged to contain a measured amount of washed and dried basic chromatographic grade alumina powder, and further characterized in that the cap contains a solid central projection which extends to a hemispherical hollow opening in which measured amount of an iron-saturating substance is bonded to the interior surface of the projection comprising the steps of:
  (a) removing the cap containing the iron-saturating substance,
  (b) adding a solvent to the tube containing the alumina followed by the sample of serum or plasma,
  (c) replacing the cap,
  (d) mixing the contents of the tube,
  (e) allowing the alumia to settle, and
  (f) measuring the iron content of the supernatant.

* * * * *